United States Patent
King

(10) Patent No.: US 11,357,837 B2
(45) Date of Patent: *Jun. 14, 2022

(54) IMPLANTABLE MATRIX HAVING OPTIMUM LIGAND CONCENTRATIONS

(71) Applicant: WARSAW ORTHOPEDIC, INC., Warsaw, IN (US)

(72) Inventor: Vanja Margareta King, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/372,064

(22) Filed: Apr. 1, 2019

(65) Prior Publication Data

US 2019/0224287 A1    Jul. 25, 2019

Related U.S. Application Data

(63) Continuation of application No. 15/645,367, filed on Jul. 10, 2017, now Pat. No. 10,265,386, which is a
(Continued)

(51) Int. Cl.
*A61K 38/18* (2006.01)
*C07K 14/51* (2006.01)
(Continued)

(52) U.S. Cl.
CPC .......... *A61K 38/4886* (2013.01); *A61K 31/00* (2013.01); *A61K 35/28* (2013.01); *A61K 38/18* (2013.01); *A61K 38/1875* (2013.01); *A61K 38/55* (2013.01); *A61K 47/50* (2017.08); *A61L 27/12* (2013.01); *A61L 27/24* (2013.01);
(Continued)

(58) Field of Classification Search
CPC ................ A61K 38/18; A61K 38/1875; A61K 38/4886; A61L 27/24; A61L 27/3834; A61L 27/54; A61L 27/56; A61L 27/58
See application file for complete search history.

(56) References Cited

U.S. PATENT DOCUMENTS 4,624,255 A    11/1986    Schenck et al.
4,863,457 A    9/1989    Lee
(Continued)

FOREIGN PATENT DOCUMENTS

WO    02100350 A2    12/2002
WO    03005961 A2    1/2003
WO    2008039173 A2    4/2008

OTHER PUBLICATIONS

Physiological Stress Responses in Bioprocesses, 2004, by S.O. Enfors, vol. 89, p. 184.*
(Continued)

*Primary Examiner* — Xiaozhen Xie
(74) *Attorney, Agent, or Firm* — Sorell, Lenna & Schmidt, LLP; William D. Schmidt, Esq.

(57) ABSTRACT

Implantable matrices and methods are provided. The matrices are configured to fit at or near a target tissue site, the matrices comprise biodegradable materials and ligands bound to the matrices and are configured to bind receptors and allow influx of cells into the implantable matrices, wherein the ratio of ligands to receptors is from about 1.5 to about 0.5.

10 Claims, 2 Drawing Sheets

Related U.S. Application Data continuation of application No. 13/017,759, filed on Jan. 31, 2011, now Pat. No. 9,717,779.

(51) Int. Cl.

| | | |
|---|---|---|
| *A61L 27/24* | (2006.01) | |
| *A61L 27/12* | (2006.01) | |
| *A61L 27/54* | (2006.01) | |
| *A61L 27/56* | (2006.01) | |
| *A61L 27/58* | (2006.01) | |
| *A61K 38/55* | (2006.01) | |
| *A61K 38/48* | (2006.01) | |
| *A61K 35/28* | (2015.01) | |
| *A61K 47/50* | (2017.01) | |
| *A61K 31/00* | (2006.01) | |
| *A61L 27/38* | (2006.01) | |
| *C08L 89/00* | (2006.01) | |

(52) U.S. Cl.
CPC ........... *A61L 27/3834* (2013.01); *A61L 27/54* (2013.01); *A61L 27/56* (2013.01); *A61L 27/58* (2013.01); *C07K 14/51* (2013.01); *C08L 89/00* (2013.01); *A61L 2300/40* (2013.01)

(56) References Cited

U.S. PATENT DOCUMENTS

| | | | |
|---|---|---|---|
| 5,522,844 A | | 6/1996 | Johnson |
| 5,853,746 A | * | 12/1998 | Hunziker ............... A61L 24/106 424/426 |
| 5,868,789 A | | 2/1999 | Huebner |
| 6,069,129 A | | 5/2000 | Sandberg et al. |
| 6,179,862 B1 | | 1/2001 | Sawhney |
| 6,287,588 B1 | | 9/2001 | Shih et al. |
| 6,331,311 B1 | | 12/2001 | Brodbeck et al. |
| 6,428,804 B1 | | 8/2002 | Suzuki et al. |
| 6,432,063 B1 | | 8/2002 | Marcus |
| 6,461,631 B1 | | 10/2002 | Dunn et al. |
| 6,491,651 B1 | | 12/2002 | Leahy et al. |
| 6,589,549 B2 | | 7/2003 | Shih et al. |
| 6,630,155 B1 | | 10/2003 | Chandrashekar et al. |
| 6,632,457 B1 | | 10/2003 | Sawhney |
| 6,696,073 B2 | | 2/2004 | Boyce et al. |
| 6,756,058 B2 | | 6/2004 | Brubaker et al. |
| 6,773,714 B2 | | 8/2004 | Dunn et al. |
| 6,863,694 B1 | | 3/2005 | Boyce et al. |
| 6,974,462 B2 | | 12/2005 | Sater |
| 7,144,412 B2 | | 12/2006 | Wolf et al. |
| 7,166,570 B2 | | 1/2007 | Hunter et al. |
| 7,220,281 B2 | | 5/2007 | Lambrecht et al. |
| 7,229,441 B2 | | 6/2007 | Trieu et al. |
| 7,235,043 B2 | | 6/2007 | Gellman et al. |
| 7,318,840 B2 | | 1/2008 | McKay |
| 7,329,259 B2 | | 2/2008 | Cragg |
| 7,361,168 B2 | | 4/2008 | Makower et al. |
| 7,367,978 B2 | | 5/2008 | Drewry et al. |
| 7,449,019 B2 | | 11/2008 | Uchida et al. |
| 7,449,559 B2 | | 11/2008 | Ward et al. |
| 7,462,155 B2 | | 12/2008 | England |
| 7,482,174 B2 | | 1/2009 | Kiefer et al. |
| 7,541,186 B2 | | 6/2009 | Reh et al. |
| 2001/0014831 A1 | | 8/2001 | Scarborough |
| 2002/0009454 A1 | | 1/2002 | Boone et al. |
| 2002/0082694 A1 | | 6/2002 | McKay |
| 2002/0090398 A1 | | 7/2002 | Dunn et al. |
| 2003/0009235 A1 | | 1/2003 | Manrique et al. |
| 2003/0133967 A1 | | 7/2003 | Ruszczak et al. |
| 2003/0204191 A1 | | 10/2003 | Sater et al. |
| 2003/0236573 A1 | | 12/2003 | Evans et al. |
| 2004/0072799 A1 | | 4/2004 | Li et al. |
| 2004/0082540 A1 | | 4/2004 | Hermida Ochoa |
| 2004/0214793 A1 | | 10/2004 | Hermida Ochoa |
| 2004/0249463 A1 | | 12/2004 | Bindseil et al. |
| 2005/0025809 A1 | | 2/2005 | Hasirci et al. |
| 2005/0142163 A1 | | 6/2005 | Hunter et al. |
| 2005/0186261 A1 | | 8/2005 | Avelar et al. |
| 2005/0197293 A1 | | 9/2005 | Meilis et al. |
| 2006/0079773 A1 | | 4/2006 | Mourad et al. |
| 2006/0106361 A1 | | 5/2006 | Muni et al. |
| 2006/0148903 A1 | | 7/2006 | Burch et al. |
| 2006/0189944 A1 | | 8/2006 | Campbell et al. |
| 2006/0247772 A1 | | 11/2006 | McKay |
| 2006/0270037 A1 | | 11/2006 | Kato et al. |
| 2006/0293757 A1 | | 12/2006 | McKay et al. |
| 2007/0010440 A1 | * | 1/2007 | Schense ............... A61L 27/225 514/8.8 |
| 2007/0077267 A1 | | 4/2007 | Molz, IV et al. |
| 2007/0142916 A1 | | 6/2007 | Olson, Jr. et al. |
| 2007/0156180 A1 | | 7/2007 | Jaax et al. |
| 2007/0185367 A1 | | 8/2007 | Abdou |
| 2007/0185497 A1 | | 8/2007 | Cauthen et al. |
| 2007/0202074 A1 | | 8/2007 | Shalaby |
| 2007/0243225 A1 | | 10/2007 | McKay |
| 2007/0243228 A1 | | 10/2007 | McKay |
| 2007/0259019 A1 | | 11/2007 | McKay |
| 2008/0008988 A1 | | 1/2008 | McKay et al. |
| 2008/0019969 A1 | | 1/2008 | Gorman |
| 2008/0019970 A1 | | 1/2008 | Gorman |
| 2008/0019975 A1 | | 1/2008 | Gorman |
| 2008/0069852 A1 | * | 3/2008 | Shimp et al. ............ 424/423 |
| 2008/0091207 A1 | | 4/2008 | Truckai et al. |
| 2008/0147197 A1 | * | 6/2008 | McKay ............ 623/23.51 |
| 2008/0175911 A1 | | 7/2008 | McKay et al. |
| 2008/0213283 A1 | | 9/2008 | Olmarker et al. |
| 2008/0294261 A1 | | 11/2008 | Pauza et al. |
| 2008/0317805 A1 | | 12/2008 | McKay et al. |
| 2009/0024135 A1 | | 1/2009 | Triplett et al. |
| 2010/0047350 A1 | | 2/2010 | McKay |
| 2010/0049322 A1 | | 2/2010 | McKay |
| 2010/0226959 A1 | | 9/2010 | McKay |
| 2011/0182962 A1 | * | 7/2011 | McKay ............... A61L 27/446 424/423 |

OTHER PUBLICATIONS

McGuire et al., J. Histochem. Cytochem., 2012, vol. 60(3):243-253.*

Kim et al., Agric. Biol. Chem., 1983, vol. 47, No. 11, pp. 2655, 2666 and 2667 (3 pages).*

Li et al., Arch. Ophthalmol., 2001, vol. 119(1):71-78.*

* cited by examiner

IMPLANTABLE MATRIX HAVING OPTIMUM LIGAND CONCENTRATIONS

BACKGROUND

Implantable matrices have been used extensively to solve various medical problems in human and animal orthopedic surgical practices and their application has also extended to the field of cosmetic and reconstructive surgery, dental reconstructive surgery, and other medical fields involving surgery of hard and soft tissues.

Often times, to enhance growth of different cells within the implantable matrix and repair of tissue, a ligand is disposed on the implantable matrix and becomes available so that it can interact with a particular target receptor and cause the desired biological function. The formation and dissociation of specific noncovalent interactions between a ligand and its receptor plays a crucial role in the function of biological systems. The ligand and/or receptor of the matrix, in some embodiments, can stimulate other mammalian cell growth, such as for example, myocytes, cardiocytes to repair heart tissue, neuronal cells, or the like.

For example, when dealing with a ligand, such as bone morphogenic protein (BMP), it can be disposed on an implantable matrix and placed in a bone defect. BMP can be applied to the matrix before, during or after implantation. The BMP interacts with specific receptors on the cell surface, referred to as bone morphogenetic protein receptors (BMPRs). As persons of ordinary skill are aware the BMP spur the patient's body to begin the formation of new bone and/or cartilage growth. The BMP acts much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. In this manner severe fractures may be healed, and vertebrae successfully fused.

Signal transduction through BMPRs also results in mobilization of members of the SMAD family of proteins. The signaling pathways involving BMPs, BMPRs and SMADs are also important in the development of the heart, and central nervous system tissue, as well as bone and cartilage.

Sometimes when too much ligand is applied to the matrix, or the surgeon manipulates the matrix to place it in the defect, excessive compression occurs causing increased amounts of ligand (e.g., bone morphogenic protein, TGF-alpha, TGF-beta, EGF, etc.) to leak from the matrix, which may reduce the stable microenvironment for cell growth, cause off target side effects (e.g., unwanted cell growth in other areas) or inhibit biological activity via a feedback inhibition. Sometimes too little ligand is applied to the matrix or the ligand on or in the matrix is depleted, which may also reduce the stable microenvironment for cell growth. Thus, there is a need to develop new matrices that have optimum ligand receptor concentrations.

SUMMARY

Implantable matrices are provided that improve efficacy and maintain a stable microenvironment for cell growth. By maintaining a ligand to receptor ratio of from about 0.5 to about 1.5 a stable microenvironment for cell growth can be achieved. In some embodiments, the implantable matrices provided minimize off target side effects and reduce unwanted feed back inhibition.

In some embodiments, the matrix comprises bone morphogenic protein, and maintains a ligand to receptor ratio of from about 0.5 to about 1.5, which will reduce excess ligand from being forced out of the matrix into the surrounding environment, which may lead to unwanted adverse events such as local transient bone resorption.

In some embodiments, there is an implantable matrix configured to fit at or near a target tissue site, the matrix comprising: a biodegradable material and a ligand bound to the matrix and configured to bind a receptor and allow influx of cells into the implantable matrix, wherein the ratio of ligand to receptor is from about 0.5 to about 1.5.

In some embodiments, there is a method for treating a target tissue site beneath the skin in a patient in need of such treatment, the method comprising administering an implantable matrix configured to fit at or near a target tissue site, the matrix comprising: a biodegradable collagen and a ligand comprising bone morphogenic protein bound to the matrix and configured to bind a receptor of progenitor, bone and/or cartilage cells and allow influx of the cells into the implantable matrix, wherein the ratio of ligand to receptor is from about 0.5 to about 1.5.

In some embodiments, there is a method of making an implantable matrix configured to fit at or near a target tissue site, the method comprising providing a biodegradable material and applying a ligand to bind the ligand to the matrix, the matrix configured to bind a receptor and allow influx of cells into the implantable matrix, wherein the ligand is applied to the matrix in an amount where the ratio of ligand to receptor is from about 0.5 to about 1.5.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
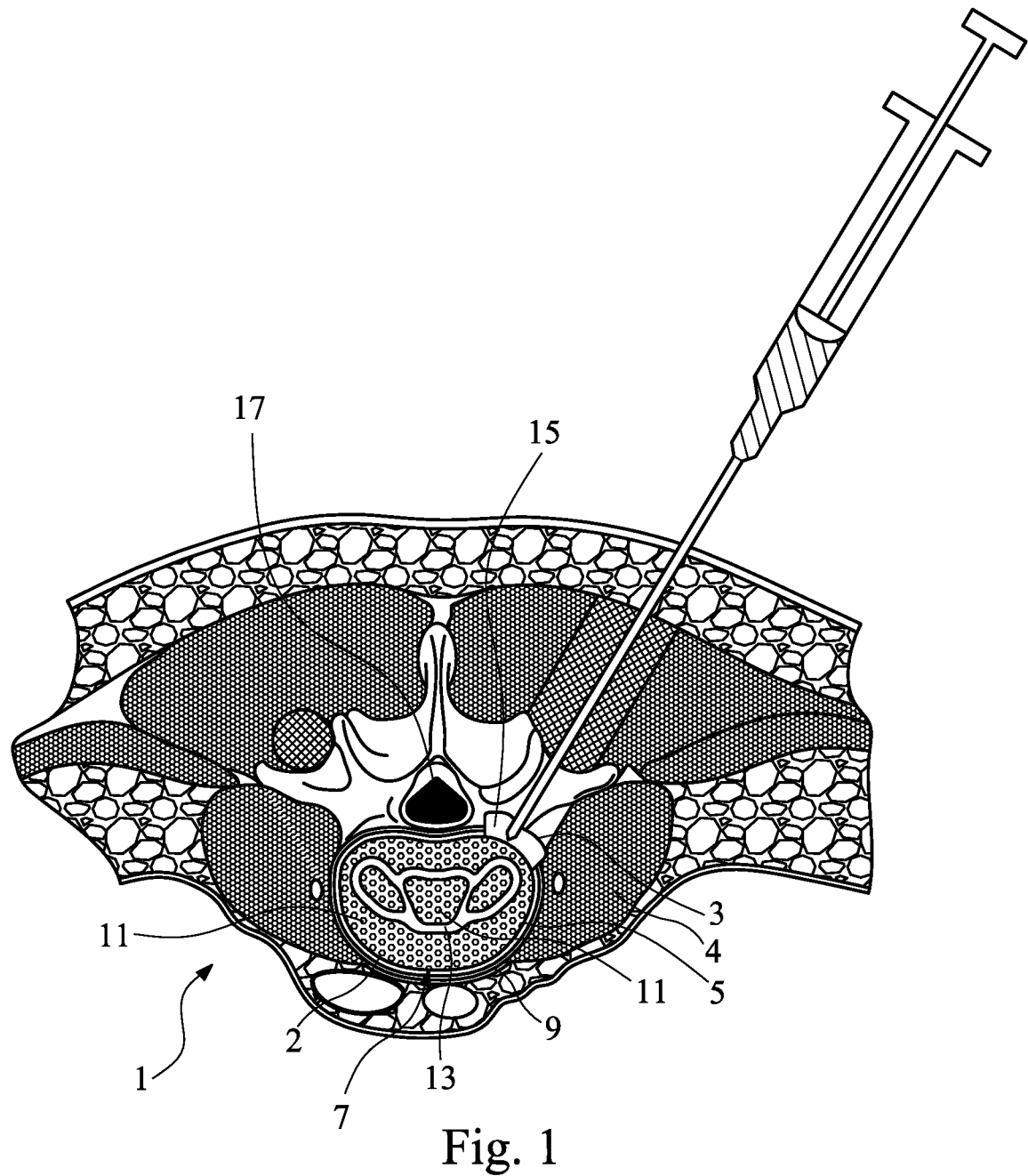
FIG. 1 illustrates an axial cross-sectional view of the implantable matrix being injected at a target tissue site and the optimum ligand concentration being placed in the matrix.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations; the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:

Definitions

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the matrix will degrade over time by the action of enzymes, by hydrolytic action and/or by other similar mechanisms in the human body. In various embodiments, "biodegradable" includes that a matrix (e.g., sponge, sheet, etc.) can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" or "bioresorbable" it is meant that the matrix will be broken down and absorbed within the human body, for example, by a cell or tissue. "Biocompatible" means that the matrix will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

The term "resorbable" includes biologic elimination of the products of degradation by metabolism and/or excretion over time, for example, usually months.

The term "particle" refers to pieces of a substance of all shapes, sizes, thickness and configuration such as fibers, threads, narrow strips, thin sheets, clips, shards, etc., that posses regular, irregular or random geometries. In some embodiments, the particles are elongated having more length than width (e.g., long and slender particles). It should be understood that some variation in dimension will occur in the production of the particles and particles demonstrating such variability in dimensions are within the scope of the present application.

The term "target tissue site" is intended to mean the location of the tissue to be treated. Typically the placement site of the matrix will be the same as the target site to provide for optimal targeted drug delivery. However, the present application also contemplates positioning the matrix at a placement site at or near the target site such that the ligand (e.g., growth factor, other therapeutic agent) can be delivered to the surrounding vasculature, which carries the agent to the desired nearby target site. As used herein, the term "at or near" includes embodiments where the placement site and target site are within close proximity (e.g., within about 1 mm to 5 cm).

The term "autograft" as utilized herein refers to tissue that is extracted from the intended recipient of the implant. These include elongated particles.

The term "allograft" as utilized herein refers to tissue intended for implantation that is taken from a different member of the same species as the intended recipient. These include elongated particles.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable. These include elongated particles.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here in anyway whatsoever. These include elongated particles.

The expressions "whole bone" and "substantially fully mineralized bone" refer to bone containing its full or substantially full, original mineral content that can be used. This type of bone can be used to make elongated particles.

The expression "demineralized bone" includes bone that has been partially, fully, segmentally or superficially (surface) demineralized. This type of bone can be used to make elongated particles.

The expression "substantially fully demineralized bone" as utilized herein refers to bone containing less than about 8% of its original mineral context. This type of bone can be used to make elongated particles.

A "therapeutically effective amount" or "effective amount" is such that when administered, the ligand (e.g., drug, growth factor, etc.) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the ligand's administered pharmacokinetic properties, the route of administration, patient conditions and characteristics (sex, age, body weight, health, size, etc.), extent of symptoms, concurrent treatments, frequency of treatment and the effect desired. In some embodiments the implantable matrix is designed for sustained release. In some embodiments, the implantable matrix comprises an effective amount of a ligand that is based on a ratio of ligand to receptor. In some embodiments, the ratio of ligand to receptor is from about 0.5 to about 1.5.

The phrase "immediate release" is used herein to refer to one or more ligand(s) (e.g., therapeutic agent(s)) that is introduced into the body and that is allowed to dissolve in or become absorbed at the location to which it is administered, with no intention of delaying or prolonging the dissolution or absorption of the drug.

The phrases "prolonged release", "sustained release" or "sustain release" (also referred to as extended release or controlled release) are used herein to refer to one or more ligand(s) (e.g., therapeutic agent(s)) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix and/or component thereof, or as the result of metabolic transformation or dissolution of the therapeutic agent(s) or conjugates of therapeutic agent(s). The release need not be linear and can be pulse type dosing.

The "matrix" of the present application is utilized as a scaffold for bone and/or cartilage repair, regeneration, and/or augmentation. Typically, the matrix provides a 3-D matrix of interconnecting pores, which acts as a pliant scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable.

In some embodiments, the matrix can be shaped. The term "shaped" includes that the matrix including the elongated particles is formed into sheets, plates, disks, cones, pins, screws, tubes, teeth, bones, portion of bone, wedges, cylinders, threaded cylinders, and the like, as well as more complex geometric configurations.

The terms "treating" and "treatment" when used in connection with a disease or condition refer to executing a protocol that may include a repair procedure (e.g., osteochondral repair procedure), administering one or more matrices to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the implantable matrix can be used to treat subchondral, osteochondral, hyaline cartilage and/or condyle defects.

The term "subchondral" includes an area underlying joint cartilage. The term "subchondral bone" includes a very dense, but thin layer of bone just below a zone of cartilage and above the cancellous or trabecular bone that forms the bulk of the bone structure of the limb. "Osteochondral" includes a combined area of cartilage and bone where a lesion or lesions can occur. "Osteochondral defect" includes a lesion, which is a composite lesion of cartilage and subchondral bone. "Hyaline cartilage" includes cartilage containing groups of isogenous chondrocytes located within lacunae cavities which are scattered throughout an extracellular collagen matrix. A "condyle" includes a rounded articular surface of the extremity of a bone.

The matrix may be osteogenic. The term "osteogenic" as used herein includes the ability of the matrix to enhance or accelerate the growth of new bone tissue by one or more mechanisms such as osteogenesis, osteoconduction and or osteoinduction. In some embodiments, the matrix is osteogenic and can be delivered to other surgical sites, particularly sites at which bone growth is desired. These include, for instance, the repair of spine (e.g., vertebrae fusion) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example.

The matrix may be osteoinductive. The term "osteoinductive" as used herein includes the ability of a substance to recruit cells from the host that have the potential for forming new bone and repairing bone tissue. Most osteoinductive materials can stimulate the formation of ectopic bone in soft tissue.

The matrix may be osteoconductive. The term "osteoconductive" as utilized herein includes the ability of a non-osteoinductive substance to serve as a suitable template or substrate along which bone may grow.

The matrix may be implantable. The term "implantable" as utilized herein refers to a biocompatible device retaining potential for successful placement within a mammal. The expression "implantable device" and expressions of like import as utilized herein refers to any object implantable through surgery, injection, or other suitable means whose primary function is achieved either through its physical presence or mechanical properties.

The term "carrier" includes a diluent, adjuvant, buffer, excipient, or vehicle with which a composition can be administered. Carriers can include sterile liquids, such as, for example, water and oils, including oils of petroleum, animal, vegetable or synthetic origin, such as, for example, peanut oil, soybean oil, mineral oil, sesame oil, or the like. The growth factor may include a carrier.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g, zinc sulfate), thimerosal, methylparaben, propylparaben, carboxymethylcellulose, chlorobutanol, or heparin. The growth factor may include an excipient.

The term "lyophilized" or "freeze-dried" includes a state of a substance that has been subjected to a drying procedure such as lyophilization, where at least 50% of moisture has been removed. The matrix and/or ligand may be lyophilized or freeze-dried.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP. The ligand and/or matrix may have preservatives or be preservative free.

As used herein, the term "ligand" refers to a molecule that can selectively bind to a receptor. The term selectively means that the binding interaction is a specific interaction as opposed to a non-specific interaction. A ligand can be a peptide, polypeptide, nucleic acid, carbohydrate, lipid, or any organic derived compound. Moreover, derivatives, analogues and mimetic compounds are also intended to be included within the definition of this term. As such, a molecule that is a ligand can also be a receptor and, conversely, a molecule that is a receptor can also be a ligand since ligands and receptors are defined as binding partners. Specific examples of ligands are natural or synthetic organic compounds as well as recombinantly or synthetically produced polypeptides. For example, ligands include, but are not limited to, BMP (bone morphogenetic protein), BMP-2 (bone morphogenetic protein), bFGF (basic fibroblast growth factor), IGF-1 (insulin-like growth factor), PDGF (platelet-derived growth factor), rhBMP (human recombinant bone morphogenetic protein), TGF-β 1 (transforming growth factor beta 1), VEGF (vascular endothelial growth factor), GDf (growth and differentiation factor), and any combinations thereof. The ligand is the binding partner of the receptor.

As used herein, the term "polypeptide" when used in reference to a receptor or a ligand is intended to refer to peptide, polypeptide or protein of two or more amino acids. The term is similarly intended to refer to derivatives, analogues and functional mimetics thereof. For example, derivatives can include chemical modifications of the polypeptide such as alkylation, acylation, carbamylation, iodination, or any modification which derivatizes the polypeptide. Analogues can include modified amino acids, for example, hydroxyproline or carboxyglutamate, and can include amino acids that are not linked by peptide bonds. Mimetics encompass chemicals containing chemical moieties that mimic the function of the polypeptide regardless of the predicted three-dimensional structure of the compound. For example, if a polypeptide contains two charged chemical moieties in a functional domain, a mimetic places two charged chemical moieties in a spatial orientation and constrained structure so that the charged chemical function is maintained in three-dimensional space. Thus, all of these modifications are included within the term "polypeptide" so long as the polypeptide retains its binding function.

As used herein, the term "receptor" is intended to refer to a molecule of sufficient size so as to be capable of selectively binding a ligand. Such molecules generally are macromolecules, such as polypeptides, nucleic acids, carbohydrate or lipid. However, derivatives, analogues and mimetic compounds as well as natural or synthetic organic compounds are also intended to be included within the definition of this term. The receptor can be a fragment of the entire molecule so long as it exhibits selective binding to a desired ligand. For example, if the receptor is a polypeptide, a fragment or domain of the native polypeptide which maintains substantially the same binding selectivity as the intact polypeptide is intended to be included within the definition of the term receptor. Specific examples of such a binding domain or fragment is the variable region of an antibody molecule. Complementarity determining regions (CDR) within the variable region can also exhibit substantially the same binding selectivity as the antibody molecule and are therefore considered to be within the meaning of the term. The receptor is the binding partner of the ligand.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Implantable matrices are provided that improve efficacy and maintain a stable microenvironment for cell growth. By maintaining a ligand to receptor ratio of from about 0.5 to about 1.5 a stable microenvironment for cell growth can be achieved. In some embodiments, the implantable matrices provided minimize off target side effects and reduce unwanted feed back inhibition.

In some embodiments, the matrix comprises bone morphogenic protein, and maintains a ligand to receptor ratio of from about 0.5 to about 1.5, which will reduce excess ligand from being forced out of the matrix into the surrounding environment, which may lead to unwanted adverse events such as local transient bone resorption.

In some embodiments, the growth factor (e.g., rhBMP-2) will be more evenly distributed throughout the interior of the matrix and facilitate more uniform bone growth throughout the whole matrix. In some embodiments, the growth factor (e.g., rhBMP-2) is temporarily retained within the matrix so as to limit new bone formation to within the matrix.

The headings below are not meant to limit the disclosure in any way; embodiments under any one heading may be used in conjunction with embodiments under any other heading.

Matrix

The matrix provides a tissue scaffold for the cells to guide the process of tissue formation in vivo in three dimensions. The morphology of the matrix guides cell migration and cells are able to migrate into or over the matrix. The cells then are able to proliferate and synthesize new tissue and form bone and/or cartilage. In some embodiments, one or more tissue matrices are stacked on one another.

The matrix is porous and configured to allow influx of at least bone and/or cartilage cells therein. In some embodiments, the matrix is also configured to release a ligand. By porous is meant that the matrix has a plurality of pores. The pores of the matrix are a size large enough to allow influx of blood, other bodily fluid, and progenitor and/or bone and/or cartilage cells into the interior to guide the process of tissue formation in vivo in three dimensions.

In some embodiments, the matrix comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue. In some embodiments, the matrix contains one or more ligands bound in or on its surface.

In some embodiments, the porous interior can hold the ligand within the matrix and because the interior is porous, the ligand is evenly distributed throughout the matrix when growth factor is injected into the matrix.

In some embodiments, the ligand (e.g., growth factor) will be held within the interior of the matrix and released into the environment surrounding the matrix (e.g., bone defect, osteochondral defect, etc.) as the matrix degrades over time In some embodiments, the matrix comprises biodegradable polymeric and non-polymeric material. For example, the matrix may comprises one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix can be designed to be compression resistant and has elongated particles uniformly or randomly distributed throughout it, and the matrix is substantially rigid and resists compression. For example, in some embodiments, the matrix may have a modulus of elasticity between 1.0 MPa and 20.0 MPa, or 2.0 MPa and 10.0 MPa or between 3.0 MPa and 5.0 MPa, with the higher MPa values obtainable by cross-linking.

In some embodiments, the matrix (e.g., exterior and/or interior) comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone and/or cartilage will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®. marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

Compression resistance is needed for many tissue engineering applications such as tibial plateau fractures, acetabular defects, long bone comminuted fractures, oral maxillofacial defects, spinal fusions, and cartilage subchondral defects. Compression resistant matrices will help facilitate adequate volumes of newly formed bone.

In some embodiments, the matrix is compression resistant where the matrix resists reduction in size or an increase in density when a force is applied as compared to matrices without the elongated particles disposed in it. In various embodiments, the matrix resists compression by at 10%, 15%, 20%, 25%, 30%, 35%, 40%, 45%, 50%, 55%, 60%, 65%, 70%, 75%, 80%, 85%, 90%, 95%, or more in one or all directions when a force is applied to the matrix.

Ligands

Ligands include a substance that forms a complex with a biomolecule to serve a biological purpose. In some embodiments, a ligand can act as a signaling triggering biomolecule, binding to a site on a target protein. The binding may occur by intermolecular forces, such as ionic bonds, non-covalent bonds, hydrogen bonds and/or van der Waals forces. The binding is usually reversible. Ligand binding to a receptor alters the chemical conformation, that is the three dimensional shape of the receptor. The conformational state of a receptor determines the functional state of a receptor.

In some embodiments, a ligand and/or therapeutic agent may be disposed on or in the matrix by hand, electrospraying, ionization spraying or impregnating, lyophilization, vibratory dispersion (including sonication), nozzle spraying, compressed-air-assisted spraying, injecting, brushing, soaking and/or pouring. For example, in some embodiments, when the ligand is a growth factor such as rhBMP-2, it may be disposed on or in the biodegradable matrix by the surgeon before the biodegradable matrix is administered or the matrix may be pre-loaded with the growth factor by the manufacturer beforehand.

Ligands can be for example, small molecules, peptides, growth factors, cytokines, ligands, hormones, and other molecules that regulate growth and/or differentiation. The ligand can be captured from an autologous source, be obtained from a commercial source, or can be manufactured (e.g., by recombinant procedures).

Examples of ligands that can be applied to or in the matrix include, but are not limited to, FGF, IGF, interleukins, IL-I, IL-11, TGF, NGF, EGF, HGF, simvastatsin, dexamethasone, oxysterols, sonic hedgehog, interferon, fibronectin, "RGD" or integrin peptides and/or protein, keratinocyte growth factor, osteogenic proteins, MSX1, NFKB1, RUNX2, SMAD1, SMAD2, SMAD3, SMAD4, SOX9, TNF, TWIST1, VDR, AHSG, AMBN, AMELY, BGLAP, ENAM, MINPP1, STATH, TUFT1, COL11A1, SOX9, ALPL, AMBN, AMELY, BGLAP, CALCR, CDH11, DMP1, DSPP, ENAM, MINPP1, PHEX, RUNX2, STATH, TFIP11, TUFT1, BGLAP, COL10A1, COL12A1, COL1A1, COL1A2, COL2A1, COMP, FGFR1, IGF1, IGF2, MSX1, ANXAS, CALCR, CDH11, COMP, DMP1, EGF, MMP2, MMP8, COL10A1, COL14A1, COL15A1, COL3A1, COL4A3, COL5A1, EGFR, FGF1, FGF3, IGF1R, CSF3, FLT1, IGF1, IGF1, IGF2, PDGFA, SMAD3, TGFB1, TGFB2, TGFB3, TGFBR2, CSF2, CSF3, FGFR1, FGFR2, FLT1, GDF10, IGF1, IGF1R, IGF2, PDGFA, TGFB1, TGFB2, TGFB3, TGFBR1, TGFBR2, VEGFA, VEGFB, AHSG, SERPINH1, CTSK, MMP10, MMP9, PHEX, AMBN, AMELY, ENAM, STATH, TUFT1, BGN, COMP, DSPP, GDF10, CDH11, ICAM1, ITGB1, VCAM1, ITGA1, ITGA2, ITGA3, ITGAM, ITGB1, CD36, COMP, SCARB1, AMH, GDF2 (BMP9), GDF3 (Vgr-2), GDF5 (CDMP-1), GDF6, GDF7, IGFBP3, IL6, INHA (inhibin a), INHBA (inhibin BA), LEFTY1, LTBP1, LTBP2, LTBP4, NODAL, ACVR1 (ALK2), ACVR2A, ACVRL1 (ALK1), AMHR2, BMPR1A (ALK3), BMPR1B (ALK6), BMPR2, ITGB5 (integrin B5), ITGB7 (integrin B7), LTBP1, NR0B1, STAT1, TGFB1I1, TGFBR1, (ALK5) TGFBR2, TGFBR3, TGFBRAP1, CDC25A, CDKN1A (p21WAF1/p21CIP1), CDKN2B (p15LNK2B), FOS, GSC (goosecoid), IGFBP3, ITGB5 (integrin B5), ITGB7 (integrin B7), JUN, JUNB, MYC, SERPINE 1 (PAI-1), TGFB1I1, TSC22D1 (TGFB1I4), TGIF1, DLX2, ID1, ID2, JUNB, SOX4, STAT1, BAMBI, BMPER, CDKN2B (p15LNK2B), CER1 (cerberus), CHRD (chordin), CST3, ENG (Evi-1), EVIL FKBP1B, HIPK2, NBL1 (DAN), NOG, PLAU (uPA), RUNX1 (AML1), SMURF1 and other molecules that regulate growth or differentiation, as well as combinations of these ligands.

The biodegradable matrix may comprise at least one ligand that is a growth factor. These growth factors include osteoinductive agents (e.g., agents that cause new bone growth in an area where there was none) and/or osteoconductive agents (e.g., agents that cause ingrowth of cells into and/or through the matrix). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a matrix are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are loaded in the matrix include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the matrix further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the matrix include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the matrix include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the matrix include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the matrix include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the matrix include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the matrix include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the matrix are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, the ligand is BMP-2, BMP-7 and/or GDF-5 and may be used at 1-2 mg/cc of matrix. The concentrations of ligand can be varied based on the desired length or degree of osteogenic effects desired. However, the optimum ratio of ligand to receptor should be from about 0.5 to about 1.5 or from about 0.7 to about 1.0 so that the ligand works with optimum efficacy.

Similarly, one of skill in the art will understand that the duration of sustained release of the ligand can be modified by the manipulation of the compositions of the matrix, such as for example, microencapsulation of the ligand within polymers. The sustained release matrix can therefore be designed to provide customized time release of ligand that stimulate the natural healing process.

The ligand may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the ligand may comprise sterile and/or preservative free material.

These above inactive ingredients may have multi-functional purposes including the carrying, stabilizing and controlling the release of the ligand and/or other therapeutic agent(s). The sustained release process, for example, may be by a solution-diffusion mechanism or it may be governed by an erosion-sustained process.

In some embodiments, a pharmaceutically acceptable formulation comprising a ligand is provided, wherein the formulation is a freeze-dried or lyophilized formulation, alone or in combination with the matrix. Typically, in the freeze-dried or lyophilized formulation an effective amount of a ligand is provided. Lyophilized formulations can be reconstituted into solutions, suspensions, emulsions, or any other suitable form for administration or use. The lyophilized formulation may comprise the liquid used to reconstitute the ligand. Lyophilized formulations are typically first prepared as liquids, then frozen and lyophilized. The total liquid volume before lyophilization can be less, equal to, or more than the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the ligand are typically reconstituted for use by addition of an aqueous solution to dissolve the lyophilized formulation. A wide variety of aqueous solutions can be used to reconstitute a lyophilized formulation. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

The matrix can also include a protease inhibitor to minimize degradation of the ligand and/or receptor. Protease inhibitors include saquinavir, indinavir, ritonavir, nelfinavir, amprenavir, lopinavir, atazanavir, fosamprenavir, tipranavir, darunavir, metalloprotease, MMP-1 (collagenase-1), MMP-9, MMP-7 (matrilysin), MMP-8 (collagenase-2), MMP-13 (collagenase-3), MMP-18 (collagenase-4), MMP-2 (gelatinase a), MMP-9 (gelatinase b), MMP-3 (stromelysin-1), MMP-10 (stromelysin-2), MMP-11 (stromelysin-3), MMP-7 (matrilysin), MMP-26 (matrilysin), MMP-12 (metalloelastase), MMP-14 (MT1-MMP), MMP-15 (MT2-MMP), MMP-16 (MT3-MMP), MMP-17 (MT4-MMP), MMP-24 (MT5-MMP) transmembrane, MMP-25 (MT6-MMP), gpI anchor, MMP-19, MMP-20 (enamelysin), MMP-x, MMP-23, MMP-27, MMP-28 (epilysin), serine protease inhibitors, such as for example, batimastat, aprotinin, or the like.

In various embodiments, the protease inhibitor can be in the matrix in an amount from approximately 0.0005 to approximately 100 μg/day to reduce degradation of the ligand and/or receptor. Other concentrations of the protease inhibitor include from approximately 0.0005 to approximately 50 μg/day; approximately 0.0005 to approximately 25 μg/day; approximately 0.0005 to approximately 10 μg/day; approximately 0.0005 to approximately 5 ng/day; approximately 0.0005 to approximately 1 μg/day; approximately 0.0005 to approximately 0.75 μg/day; approximately 0.0005 to approximately 0.5 μg/day; approximately 0.0005 to approximately 0.25 μg/day; approximately 0.0005 to approximately 0.1 μg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of fluocinolone is from approximately 0.001 to approximately 15 µg/day. In another embodiment, the protease inhibitor can be in a concentration in the matrix in an amount of from approximately 0.001 to approximately 10 µg/day or approximately 0.001 to approximately 5 µg/day or from approximately 0.001 to 2.5 µg/day or between 40 and 600 ng/day or between 200 and 400 µg/day.

In some embodiments, if the protease inhibitor is an inorganic enzyme inhibitor, such for example, calcium the wide range of concentration could be used for example, the protease inhibitor can be in the matrix in an amount of 0.1%, 0.25%, 0.5%, 1.0%, 2.0%, 2.5%, 3%, 4%, 5%, 10%, 15%, 20%, 25%, 30%, 35%, 40%, 45%, 50% by weight based on the total weight of the matrix to reduce the ligand and/or receptor degradation. In some embodiments, the protease inhibitor can be organic (e.g., aprotinin) and be in the matrix in an amount of from about 1 mM, 1.5 mM, 2 mM, 3 mM, or 5 mM, to about 0.1% by weight to reduce degradation of the ligand and/or receptor.

In various embodiments, the protease inhibitor reduces degradation of the ligand by about 5%, 10%, 15%, 20%, 25%, 30%, 35%, 40%, 45%, 50%, 55%, 60%, 65%, 70%, 75%, 80%, 85%, 90%, 95%, or more so that the ligand lasts from 7, 10, 14, 30, 45, 60, 90, 180 days or longer.

Ligand Receptor Interactions

Receptors can include, for example, cell surface receptors such as G protein coupled receptors, integrins, growth factor receptors (e.g., BMPRs), cytokine receptors, or can be the binding partner for the ligand. Receptors can include antibodies, other polypeptides or ligands of the immune system. Such other polypeptides of the immune system include, for example, T cell receptors (TCR), major histocompatibility complex (MHC), CD4 receptor or CD8 receptor. Furthermore, cytoplasmic receptors such as steroid hormone receptors and DNA binding polypeptides such as transcription factors and DNA replication factors are likewise included.

A ligand generally interacts with a receptor through multiple molecular interactions resulting from multiple contact points or through multiple interactions of a chemical functional group that can be described, for example, as three points. These three points can be, for example, three distinct chemical groups that serve as contact points for the binding partner. Likewise, three different amino acids or three different clusters of amino acids in a polypeptide ligand or receptor can serve as contact points for the binding partner. In this case, binding between the ligand and receptor may occur when all three points can bind.

A receptor can be any molecule that binds to a ligand. The receptors can be, for example, cell surface receptors that transmit intracellular signals upon binding of a ligand. For example, the G protein coupled receptors span the membrane seven times and couple signaling to intracellular heterotrimeric G proteins. G protein coupled receptors participate in a wide range of physiological functions, including hormonal signaling, vision, taste and olfaction. Moreover, these receptors encompass a large family of receptors, including receptors for acetylcholine, adenosine and adenine nucleotides, beta-adrenergic ligands such as epinephrine, angiotensin, bombesin, bradykinin, cannabinoids, chemokines, dopamine, endothelin, histamine, melanocortins, melanotonin, neuropeptide Y, neurotensin, opioid peptides, platelet activating factor, prostanoids, serotonin, somatostatin, tachykinin, thrombin and vasopressin, among others.

Other cell surface receptors have intrinsic tyrosine kinase activity and include growth factor or hormone receptors for ligands such as platelet-derived growth factor, epidermal growth factor, insulin, insulin-like growth factor, hepatocyte growth factor, and other growth factors and hormones. In addition, cell surface receptors that couple to intracellular tyrosine kinases include cytokine receptors such as those for the interleukins and interferons.

For example, when dealing with a ligand, such as bone morphogenic protein (BMP), BMP interacts with specific receptors on the cell surface, referred to as bone morphogenetic protein receptors (BMPRs). As persons of ordinary skill are aware the BMP spur the patient's body to begin the formation of new bone and/or cartilage. The BMP acts much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. In this manner severe fractures may be healed, and vertebrae successfully fused. Signal transduction through BMPRs results in mobilization of members of the SMAD family of proteins. The signaling pathways involving BMPs, BMPRs and SMADS are also important in the development of the heart, and central nervous system tissue, as well as bone and cartilage.

Other types of receptors include integrins. For example, integrins are cell surface receptors involved in a variety of physiological processes such as cell attachment, cell migration and cell proliferation. Integrins mediate both cell-cell and cell-extracellular matrix adhesion events. Structurally, integrins comprise a heterodimeric polypeptides where a single alpha chain polypeptide noncovalently associates with a single beta chain. In general, different binding specificities are derived from unique combinations of distinct alpha and beta chain polypeptides. For example, vitronectin binding integrins contain the $alpha_v$ integrin subunit and include $alpha_v$ $beta_3$, $alpha_v$ $beta_1$ and $alpha_v$ $beta_5$, all of which exhibit different ligand binding specificities.

Receptors also can function in the immune system. An antibody or immunoglobulin is an immune system receptor which binds to a ligand. The polypeptide receptor can be the entire antibody or it can be any functional fragment thereof which binds to the ligand. Functional fragments such as Fab, $F(ab)_2$, Fv, single chain Fv (scFv) and the like are included within the definition of the term antibody. The use of these terms in describing functional fragments of an antibody are intended to correspond to the definitions well known to those skilled in the art. Such terms are described in, for example, Harlow and Lane, Antibodies: A Laboratory Manual, Cold Spring Harbor Laboratory, New York (1989). As with the above terms used for describing antibodies and functional fragments thereof, the use of terms which reference other antibody domains, functional fragments, regions, nucleotide and amino acid sequences and polypeptides or peptides, is similarly intended to fall within the scope of the meaning of each term as it is known and used within the art. Such terms include, for example, "heavy chain polypeptide" or "heavy chain", "light chain polypeptide" or "light chain", "heavy chain variable region" ($V_H$) and "light chain variable region" ($V_L$) as well as the term "complementarity determining region" (CDR).

In addition to antibodies, the receptors can be T cell receptors (TCR). T cell receptors contain two subunits, alpha and beta, which are similar to antibody variable region sequences in both structure and function. In this regard, both subunits contain variable region which encode CDR regions similar to those found in antibodies (Immunology, Third Ed., Kuby, J. (ed.), New York, W.H. Freeman & Co. (1997)). The CDR containing variable regions of TCRs bind to antigens presented on the cell surface of antigen-presenting cells and are capable of exhibiting binding specificities to essentially any particular antigen.

Other exemplary receptors of the immune system which exhibit known or inherent binding functions include major histocompatibility complex (MHC), CD4 and CD8. MHC functions in mediating interactions between antigen-presenting cells and effector T cells. CD4 and CD8 receptors function in binding interactions between effector T cells and antigen-presenting cells. CD4 and CD8 also exhibit similar CDR region structure as do antibodies and TCRs sequences.

The ligand binds to its receptor and causes either directly or indirectly the biological function. The ligand can bind the receptor while it is attached to or in the matrix or alternatively it can be released from the matrix and be free at, near or in the target tissue site until it binds the receptor.

The ligand should be in or on or released from the matrix so that it improves efficacy and maintains a stable microenvironment for cell growth. By maintaining a ligand to receptor ratio of from about 0.5 to about 1.5 the stable microenvironment for cell growth can be achieved.

The matrix is designed to provide an optimum ligand to receptor ratio so that optimum binding is achieved. Optimum binding refers to a preferred binding characteristic of a ligand and receptor interaction. Optimum binding can be ligand-receptor interactions of a desired affinity, avidity or specificity. For example, optimum binding can be interactions that are most effective in the biological system (e.g., mammal). The optimum binding characteristics will depend on the particular application of the binding molecule. For example, the binding can be relative affinity of a ligand for the receptor. In this case, a ligand with the highest binding affinity to a receptor would have optimum binding. Optimum binding also can be binding to the largest number of receptor variants or binding to greater than some threshold number of receptor variants.

The concentration of ligand determines activity of receptors. Excess ligand is not utilized, and may actually decrease endogenous ligand and other activities in a feed-back inhibition mechanism. In some embodiments, the ratio of ligand to receptor for most optimum binding and efficiency is at or below 1.5 or 1. For example, in some embodiments, picking an average of 45,000 to 50,000 receptors per cell, a steady state capture rate of ligand to receptor of about 0.8 appears to be optimal.

In some embodiments, the receptors are cell surface receptors disposed in or on progenitor, bone and/or cartilage cells.

In some embodiments, the concentration of ligand such as BMPs, other TGF-beta ligands, TGF-alpha ligands, or EGF ligands on or in the matrix can provide the desired biological result such as differentiating mesenchymal stem cells into osteoblasts. The matrix allows the ligand to be available at from about 0.2 nanograms to about 20 nanograms/ml of matrix/hour. For 7 days of activity from the matrix which is sufficient to convert enough mesenchymal stem cells to osteoblasts to produce bone after maturation, and with degradation T½ of 5 minutes, $0.2 \times 20 \times 168 = 672$ ng/ml to 13,440 ng of ligand/ml of the matrix. This is 0.7 ug/ml to 14 ug of ligand per ml of matrix. The availability of ligand in or on the matrix is therefore in line with the ability of receptors to accept the ligand, and minimize feed-back inhibition and cross-activation of osteoclasts by ligand or the target cells. If the degradation rate is lower, less ligand is needed.

In some embodiments, the ligand can be replenished as it is depleted from the matrix. For examples, as the ligand gets depleted from the matrix by (i) degradation of the matrix, (ii) release of the ligand from the matrix, and/or (iii) binding of the ligand to the receptor on, near, or in the matrix, the matrix can be replenished with new ligand by injection or infusion of the ligand into or on the matrix. The injection can be via a needled or cannulated device or it can be via an infusion pump that delivers the ligand in or on the matrix. In some embodiments, the matrix can also include a protease inhibitor to minimize degradation of the ligand and/or receptor.

In some embodiments, the ligand remains in the matrix or on its surface over a period of at least 3 days to 12 months.

Method of Making Matrix

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

One form of manufacturing the matrix involves casting the matrix material in a mold. The matrix material can take on the shape of the mold such as, crescent, quadrilateral, rectangular, cylindrical, plug, or any other shape. Additionally, the surface of the mold may be smooth or may include raised features or indentations to impart features to the matrix. Features from the mold can be imparted to the matrix as the matrix material in the mold is dried. In particular aspects, a roughened or friction engaging surface can be formed on the superior surface and/or the inferior surface of the matrix body. In some embodiments, protuberances or raised portions can be imparted on the superior surface and/or the inferior surface from the mold. Such examples of protuberances or raised portions are ridges, serrations, pyramids, and teeth, or the like.

In some embodiments, in manufacturing the matrix, a mixture of the matrix material (e.g., collagen) is combined with the elongated particles and a liquid to wet the material and form a slurry. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to the molding operation. Certain liquids such as water can be removed in part or essentially completely from the formed matrix using conventional drying techniques such as air drying, heated drying, lyophilization, or the like.

In one embodiment of manufacture, a collagen mixture can be combined with a elongated particles and a liquid, desirably with an aqueous preparation, to form a slurry. Excess liquid can be removed from the slurry by any suitable means, including for example by applying the slurry to a liquid-permeable mold or form and draining away excess liquid.

Before, during or after molding, including in some instances the application of compressive force to the collagen containing material, the collagen material can be subjected to one or more additional operations such as heating, lyophilizing and/or crosslinking to make the porous collagen interior or exterior of the matrix the desired porosity. In this regard, crosslinking can be used to improve the strength of the formed matrix. Alternatively, one or more of the surface of the matrix can be crosslinked to reduce the size of the pores of the porous interior and thereby form the exterior of the matrix that is less permeable and/or less porous than the porous interior. Crosslinking can be achieved, for example, by chemical reaction, the application of energy such as radiant energy (e.g. UV light or microwave energy), drying and/or heating and dye-mediated photo-oxidation; dehydrothermal treatment; enzymatic treatment or others.

Chemical crosslinking agents will generally be preferred, including those that contain bifunctional or multifunctional reactive groups, and which react with matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In some embodiments, the matrices are formed by mixing the elongated particles in with a polymer slurry such as collagen and pouring into a shaped mold. The composite mixture is freeze dried and possibly chemically crosslinked and cut to the final desired shape.

In some embodiments, an implantable matrix is provided that is configured to fit at or near a target tissue site, the matrix comprising: collagen and a plurality of elongated mineral particles embedded within the collagen, the elongated mineral particles being entangled with each other and embedded in the collagen uniformly or randomly so as to reduce compression of the matrix, wherein the matrix allows influx of at least progenitor, bone and/or cartilage cells therein; and the matrix comprises bone morphogenic protein.

In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

The matrix of the present application may be used to repair bone and/or cartilage at a target tissue site, e.g., one resulting from injury, defect brought about during the course of surgery, infection, malignancy or developmental malformation. The matrix can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Application of the Ligand to the Matrix

Ligands can be bound to the matrix by, for example, ionic bonds, non-covalent bonds, hydrogen bonds and/or van der Waals forces. In some embodiments, the ligand is bound to the matrix by chemical and/or biological means such as for example by lyophilization, antibody, short peptides that bind the ligand, GRAS chemistry (generally regarded as safe), such as by using glutamic acid, glycine, hyaluronic acid, film forming chemicals (e.g., using biological or synthetic amines), or the like.

For example, a sterile matrix can be treated aseptically using a sterile film forming chemistry after soaking the matrix with the ligand and a dry matrix can be added to the sterile matrix surgically or by injection to load the matrix with the ligand for the desired activity. Film-forming agents that can be applied to or used in the matrix include those substances that leave a pliable, cohesive, and continuous covering on the surface of the matrix or in it. In some embodiments, the film from the film-forming agent has strong hydrophillic properties. Film-forming agents include polyvinylpyrrolidone (PVP), acrylates (e.g., polyacrylic acid), pullulan, polyvinyl alcohol, acrylamides, or copolymers thereof or mixtures thereof.

In some embodiments, the film-forming agent can be cellulose and its derivatives, chitosan, collagen, starch, modified starch, and various natural gum polymers and their derivatives, polymers and copolymers of methacrylic acid, amphiphilic copolymers such as polyethylene glycol 30-dipolyhydroxystearate, various silicone polymers and copolymers, and polyurethane or its derivatives. Film-forming agents include coatings on or in the matrix and can be applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches). The film-forming agent can also be the agent used to make the matrix as discussed above in the matrix section. The film forming agent can be in the matrix in an amount of from about 0.1%, 0.25%, 0.5%, 1.0%, 2.0%, 2.5%, 3%, 4%, or 5% wt % based on the total weight of the matrix.

In some embodiments, a therapeutic agent (including one or more ligands) may be disposed on or in the interior of the matrix by hand, electrospraying, ionization spraying or impregnating, vibratory dispersion (including sonication), nozzle spraying, compressed-air-assisted spraying, injecting, brushing, soaking, lyophilization, and/or pouring.

Application of the ligand to the matrix may occur at the time of surgery or by the manufacturer or in any other suitable manner. For example, the ligand may be further reconstituted using a syringe and the syringe can be placed into the interior of the matrix via insertion of a needle or cannula (piercing the matrix) and placing it into the interior of the matrix and injecting the ligand so it is evenly distributed throughout the porous interior.

In some embodiments, the ligand may be applied to the matrix (i.e., collagen) prior to combining the materials and forming it into the final matrix shape. Indeed, the ligand can be blended into the natural or synthetic polymer (i.e., POE) and poured into molds of the final shape of the matrix. Alternatively, the ligand, such as a bone morphogenic protein in a suitable liquid carrier, may be applied onto and/or into the porous loaded matrix after forming it into the final shape by soaking, dripping, injecting, spraying, etc.

In some embodiments, the interior of the matrix is loaded with the ligand BMP that functions as an osteoinductive factor. Indeed, the preferred osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, preferably near 1.5 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In some embodiments, the lyophilized ligand (e.g., BMP) can be disposed in a vial by the manufacturer and then the surgeon can mix the diluent with the lyophilized growth factor. The matrix then can be parenterally administered to the target tissue site. The term "parenteral" as used herein refers to modes of administration which bypass the gastrointestinal tract, and include for example, intramuscular, intraperitoneal, intrasternal, subcutaneous, intra-operatively, intrathecally, intradiscally, peridiscally, epidurally, perispinally, intraarticular or combinations thereof.

The amount of ligand, (e.g., bone morphogenic protein) may be sufficient to cause bone and/or cartilage growth. In some embodiments, the ligand is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the ligand is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

In some embodiments, upon implantation of the matrix or components that contact the matrix (e.g., plugs that are separate from the matrix on implantation), compression of the matrix is reduced or eliminated. As discussed above, if unwanted compression occurs, this causes the buffer from the ligand to leak from the matrix, which causes higher concentrations of the ligand (e.g., 2 mg to 2.5 mg of rhBMP-2 per cc of matrix) to remain on the matrix. This high concentration of ligand may lead to local transient bone resorption and excess osteoclast formation and bone breakdown. This may result in poor integration of the matrix with surrounding host tissue and a failed repair. Thus, by employing a compression resistant matrix, unwanted leakage is reduced or avoided. In some embodiments, localized release of the ligand may cause local irritation to the surrounding tissue. In some embodiments, the leaking of ligand from the matrix may reduce a stable microenvironment for new bone and/or cartilage growth. It also may cause the matrix to fail to retain its full efficacy over time to maximally promote growth at a target site.

FIG. 1 illustrates an axial cross-sectional view of the implantable matrix being injected at a target tissue site and the optimum ligand concentration being placed in the matrix. Shown is an axial view of a vertebral cross section 1 that is undergoing a spinal fusion procedure. A surgeon prepares a hole 3 in the posterior position of the outer annulus fibrosis band 5. The dimensions of the hole 3 are suitable for inserting various types of intervertebral disc implantable matrices 7. For any of these matrices 7 disclosed, or other such devices 7, the initial step is forming a hole 3 in the outer bands 5 of the annulus fibrosis 9, and the final steps involve sealing the hole 3. The matrices 7 may include ligands and, in particular, may include osteogenic growth agents such as BMP (bone morphogenetic protein) and rhBMP, particularly BMP-2 and rhBMP-2; bFGF (basic fibroblast growth factor); IGF-1 (insulin-like growth factor); PDGF (platelet-derived growth factor); TGF-beta-1 (transforming growth factor beta-1); VEGF (vascular endothelial growth factor); GDF (growth and differentiation factor); or combinations thereof.

The matrix 7 may be a combination of natural bone graft 11 and an interbody device 13, in which the bone graft material 11 or the matrix may include therapeutically effective amounts of one or more ligands. The interbody device 13 may be located where the nucleous pulposus resided, and the bone graft 11 fills the remaining area 2 of the intervertebral disc space where normally there would be natural nucleous pulposus tissue. The matrix 7 may act as a natural intervertebral disc and may provide a cushion and support for adjacent vertebrae. Although the method of the present invention refers to the matrix 7 being associated with osteoinductive factor ligands to promote bone and tissue growth between adjacent vertebrae, the matrix 7 can also be associated with other ligands.

After the surgeon inserts the various components 11, 13 and the matrix 7 into the cleaned disc space 2, the hole 3 may be closed by administering a second matrix 15 at or near the disc 4. The second matrix has disposed on or in it a ligand, in this case, BMP that delivers the BMP at a ligand to receptor ratio of from about 0.5 to 1.5. The matrix allows the ligand to be available at from about 0.2 nanograms to about 20 nanograms/ml of matrix/hour. For 7 days of activity, the matrix may be loaded with 0.7 ug/ml to 14 ug of ligand per ml of matrix. This will be sufficient to convert enough mesenchymal stem cells to osteoblasts to produce bone after maturation, and it assumes degradation half-life of 5 minutes, or 0.2×20×168=672 ng/ml to 13,440 ng of ligand/ml of the matrix. This is 0.7 ug/ml to 14 ug of ligand per ml of matrix. The availability of ligand in or on the matrix is therefore in line with the ability of receptors to accept the ligand, and minimize feed-back inhibition and cross-activation of osteoclasts by ligand or the target cells. If the degradation rate is lower, less ligand is needed. The matrix 15 is delivered to the area in or about the hole 3.

In some embodiments, the matrix 15 can be a non-porous tissue adherent gel, a bioresorbable polymer, or the like, that cures in vivo. The matrix 15 may be injected into the disc space located in the posterior section of the spine, for example the posterior region of the outer annulus fibrosis band 5 where the surgically prepared hole 3 is located, or, if the surgery is of the anterior sort, the outer anterior region of the annulus fibrosis band 5. The matrix 15 may be injected, for example, into the annular fibrosis 5 from the outer edge 9 of the annular fibrosis 5 to about 2 mm to about 5 mm into the annular fibrosis 5. This method may be well suited for interbody fusion procedures about the lumbar region of the spine 17, but it is within the scope of the invention whereby the matrix 15 can be used in other regions of the spine.

The BMP acts much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. As the ligand (e.g., BMP) is depleted from the matrix as binding occurs with the receptor BMPRs, the ligand can be replenished by injecting additional ligand into the matrix or by infusion to keep the ligand to receptor ratio of from about 0.5 to about 1.5 for optimum bone repair. Although, the spinal site is shown, it will be understood that the matrix can be used in other areas of the body and other target tissue types including bone, muscle, tendons, ligaments, blood vessels, etc.

Figure 2:
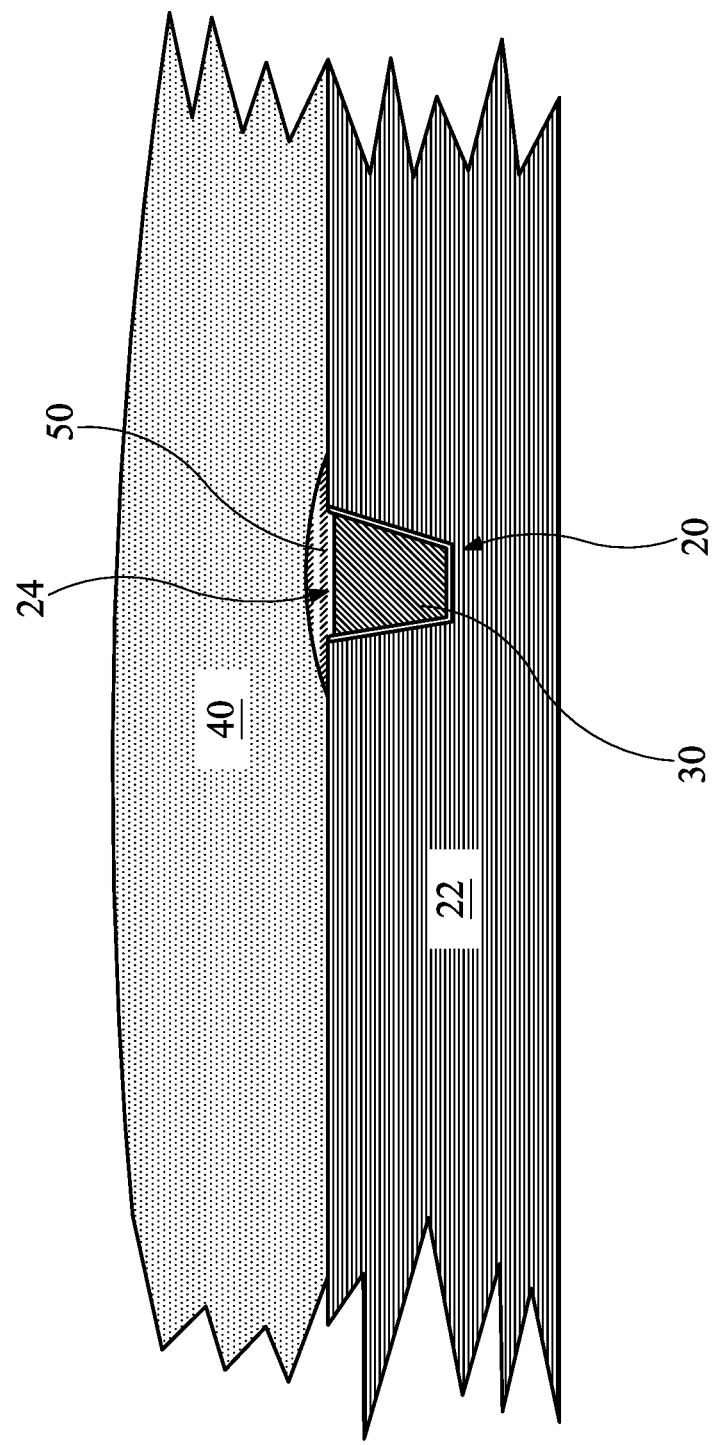
FIG. 2 illustrates a longitudinal cross-sectional view of soft tissue and sub-chondral bone where the matrix is implanted into a bone defect. The matrix contains a ligand (e.g., growth factor) that interacts with the receptors of the bone.

FIG. 2 illustrates a longitudinal cross-sectional view of soft tissue and sub-chondral bone where the matrix is implanted into a bone defect. The matrix contains a ligand (e.g., growth factor) that interacts with the receptors of the bone. A target site 20 for the matrix 30 is identified. The target site 20 may be, for example, a defect in sub-chondral bone 22. The defect 20 may be a hole created by a surgeon, trauma, disease, or otherwise. The defect is surrounded by native bone 22.

The matrix 30 comprises a ligand at a ratio of from about 0.5 to about 1.5, which is uniformly disposed in it. In some embodiments, the matrix 30 completely fills the defect 20. The matrix 30 may include, for example, therapeutically effective amounts of an osteoinductive growth factor, such as rhBMP-2, embedded within a bioresorbable scaffolding, such as a mixture of collagen and calcium phosphate. As the scaffolding is absorbed by the host bone 22, the growth factor is released at binds its receptor 24. Concentrations of the growth factor may encourage bone growth 50 within the defect 20 and/or within the matrix, thus encouraging the autologous bone 22 to migrate into and fill the defect 20. The ligand can be maintained at a ratio of from about 0.5 to about 1.5 so that optimum bone formation can occur and avoid unwanted bone formation in unwanted areas such as within local soft tissue area 40.

Elongated Particles and Stem Cells

In some embodiments, the matrix comprises elongated particles. The elongated particles offer better compression resistance because of the increased interaction of the elongated particles than conventional rounded or spherical particles. When elongated particles are embedded in a polymer matrix, the elongated particles are tethered along their length therefore resisting movement when compressed.

In some embodiments, the elongated particles comprise at least 10%, 15%, 20%, 25%, 30%, 35%, 40%, 45%, 50%, 55%, 60%, 65%, 70%, 75%, 80%, 85%, 90%, 95% by weight of the matrix. In some embodiments, the particles are predominantly elongated (powders, chips, fibers, cylinders, etc.). In some embodiments, there are non-elongated particles (e.g., rounded or spherical) in the matrix. In some embodiments, the particles in the matrix consist solely of elongated particles or non-elongated particles.

In some embodiments, the particles (bone and non-bone particles) are elongated i.e., they possess relatively high median length to median thickness ratios. In overall appearance, the elongate particles can be described as filaments, fibers, threads, slender or narrow strips, etc. Thus, e.g., the elongate particles can possess a median length of from about 2 to about 20 mm, or a median width of from about 0.02 to about 5 mm or the ratio of median length to median width is from about 10:1 to about 1000:1. In some embodiments, the elongated particles have a median length of from about 1 to about 10 mm, the median width of the elongated particles is from about 0.04 to about 2 mm and the ratio of median length to median width is from about 20:1 to about 200:1.

If desired, the elongate particles can be graded into different sizes to reduce or eliminate any less desirable size(s) of particles that may be present.

In some embodiments, the porosity of the elongated particles comprises from 0 to 50%, in some embodiments, the porosity of the elongated particles comprises 5% to 25%.

In some embodiments, the elongated particles are not entangled with each other but contact each other and portions of each elongated particle overlap in the matrix to provide compression resistance. In some embodiments, at least 50%, 55%, 60%, 65%, 70%, 75%, 80%, 85%, 90%, 95%, or more of the elongated particles overlap each other in the matrix.

In some embodiments, the elongated particles are not aggregated (e.g., they do not clump together in a mass) in the matrix.

In some embodiments, the elongated particles are randomly distributed throughout the matrix. In other embodiments, the elongated particles are uniformly or evenly distributed throughout the matrix. In some embodiments, the elongated particles may be dispersed in the matrix using a dispersing agent. In other embodiments, the elongated particles may be stirred in the polymer and the mechanical agitation will distribute the particles in the matrix until the desired distribution is reached (e.g., random or uniform).

The elongate particles can be readily obtained by any one of several methods, e.g., by milling or shaving the surface of an entire bone or relatively large section of bone. Employing a milling technique, one can obtain a mass of elongate particles containing at least about 20 weight percent of particles coming within the aforesaid range of dimensions.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the growth factor and seeded in the interior of the matrix.

In some embodiments, the elongated particles in the matrix comprise a resorbable ceramic, bone, synthetic degradable polymer, hyaluronic acid, chitosan or combinations thereof. In some embodiments, the elongated particles comprise cortical, cancellous, and/or corticocancellous, allogenic, xenogenic or transgenic bone tissue. The bone component can be fully mineralized or partially or fully demineralized or combinations thereof. The bone component can consist of fully mineralized or partially or fully demineralized bone.

In some embodiments, the matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the matrix, this will facilitate the prevention of local bone resorption by providing slower release of the growth factor due to its increased binding potential and also act as a local source of calcium and phosphate to the cells attempting to deposit new bone. The inorganic ceramic also provides compression resistance and load bearing characteristics to the matrix.

In some embodiments, the elongated particles in the matrix comprise tricalcium phosphate and hydroxyapatite in a ratio of about 80:20 to about 90:10. In some embodiments, the elongated particles in the matrix comprise tricalcium phosphate and hydroxyapatite in a ratio of about 85:15.

In some embodiments, tissue will infiltrate the matrix to a degree of about at least 50 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

In some embodiments, the matrix has a thickness of from 1 mm to 15 mm, or from about 2 mm to about 10 mm, or 3 mm to about 5 mm. Clearly, different bone defects (e.g., osteochondral defects) may require different matrices thicknesses.

In some embodiments, the matrix has a density of between about 1.6 $g/cm^3$, and about 0.05 $g/cm^3$. In some embodiments, the matrix has a density of between about 1.1 $g/cm^3$, and about 0.07 $g/cm^3$. For example, the density may be less than about 1 $g/cm^3$, less than about 0.7 $g/cm^3$, less than about 0.6 $g/cm^3$, less than about 0.5 $g/cm^3$, less than about 0.4 $g/cm^3$, less than about 0.3 $g/cm^3$, less than about 0.2 $g/cm^3$, or less than about 0.1 $g/cm^3$.

The shape of the matrix may be tailored to the site at which it is to be situated. For example, it may be in the shape of a morsel, a plug, a pin, a peg, a cylinder, a block, a wedge, a sheet, a strip, etc. The term "shape" refers to a determined or regular form or configuration in contrast to an indeterminate or vague form or configuration (as in the case of a lump or other solid mass of no special form) and is characteristic of such materials as sheets, plates, disks, cores, tubes, wedges, cylinders, or the like. This includes forms ranging from regular, geometric shapes to irregular, angled, or non-geometric shapes, or combinations of features having any of these characteristics.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect). In some embodiments, at the time of surgery, the matrix can be cut by the surgeon to the desired shape to fit the tissue or bone defect and possibly hydrated with a growth factor if necessary.

In some embodiments, there is a method for treating a target tissue site beneath the skin in a patient in need of such treatment, the method comprising administering an implantable matrix configured to fit at or near a target tissue site, the matrix comprising: a biodegradable collagen and a ligand comprising bone morphogenic protein bound to the matrix and configured to bind a receptor of progenitor, bone and/or cartilage cells and allow influx of the cells into the implantable matrix, wherein the ratio of ligand to receptor is from about 1.0 to about 0.5.

The matrices can be seeded with stem cells from any convenient source. However, stem cells that have osteogenic potential or that can be treated (e.g., differentiated) to generate cells with osteogenic potential are preferred. Sources of stem cells that can be used in the methods, devices and matrices described herein include bone marrow, adipose tissue, muscle tissue, ex vivo cultured autologous mesenchymal stem cells, allogeneic off-the-shelf mesenchymal stem cells, umbilical cord blood, embryonic yolk sac, placenta, umbilical cord, periosteum, fetal and adolescent skin, and blood. In some embodiments, the stem cells are mesenchymal stem cells or a mixture of cells that include mesenchymal stem cells (e.g., bone marrow aspirate). The stem cells can be autologous, allogeneic or from xenogeneic sources. The stem cells can be embryonic or from post-natal or adult sources.

Bone marrow aspirate is one source of stem cells useful in the methods, devices and matrices described herein. While such bone marrow aspirate can be autologous, allogeneic or from xenogeneic sources, in some embodiments the bone marrow aspirate is autologous.

Bone marrow aspirate contains a complex mixture of hematopoietic stem cells, red and white blood cells and their precursors, mesenchymal stem and progenitor cells, stromal cells and their precursors, and a group of cells including fibroblasts, reticulocytes, adipocytes, and endothelial cells which form a connective tissue network called "stroma." Cells from the stroma morphologically regulate the differentiation of hematopoietic cells through direct interaction via cell surface proteins and the secretion of growth factors and are involved in the foundation and support of the bone structure. Studies indicate that bone marrow contains "pre-stromal" cells which have the capacity to differentiate into cartilage, bone, and other connective tissue cells. Beresford "Osteogenic Stem Cells and the Stromal System of Bone and Marrow", Clin. Orthop., 240:270, 1989.

In some embodiments, the stem cells include mesenchymal stem cells. Mesenchymal stem cells can be identified by procedures available to those of skill in the art. For example, mesenchymal stem cells can be identified via colony forming unit assays (CFU-f) or via flow cytometry using markers that are typically expressed by mesenchymal stem cells. Mesenchymal stem cells generally express such markers as CD271+, CD105+, CD73+, but exhibit a CD34− and CD45− phenotype.

When bone marrow cells are employed, these cells may be obtained from iliac crest, femora, tibiae, spine, rib or other medullary spaces. In some embodiments, the stem cells are from an autologous fluid (e.g., bone marrow aspirate). Bone marrow aspirate is a good source of mesenchymal stem cells.

The stem cells can, in some embodiments, be subjected to a separation process such as centrifugation, size filtration, immunomagetic selection, etc., in order to either screen out "irrelevant" cells, and improve the efficacy of the efficacy of the mesenchymal stem cells to facitiate bone formation in implant materials. While it may not be necessary to separate the cell types and/or purify the mesenchymal stem cells, it some embodiments it may be desirable.

Additional Therapeutic Agents

The ligand of the present application may be disposed on or in the matrix with other therapeutic agents that can function as ligands or receptors. For example, the ligand may be disposed on or in the carrier by electrospraying, ionization spraying or impregnating, vibratory dispersion (including sonication), nozzle spraying, soaking, compressed-air-assisted spraying, brushing, infusion, and/or pouring.

Exemplary therapeutic agents include but are not limited to IL-1 inhibitors, such as Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin.

In various embodiments, the statin may comprise a 1:1 racemic mixture of the statin.

Kits

The matrix, ligand and devices to administer the implantable matrix composition may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

In various embodiments, a kit is provided comprising the ligand, matrix, and/or diluents. The kit may include additional parts along with the implantable matrix combined together to be used to implant the matrix (e.g., wipes, needles, syringes, etc.). The kit may include the matrix in a first compartment. The second compartment may include a vial holding the ligand, diluent and any other instruments needed for the localized drug delivery. A third compartment may include gloves, drapes, wound dressings and other procedural supplies for maintaining sterility of the implanting process, as well as an instruction booklet, which may include a chart that shows how to implant the matrix after reconstituting the growth factor. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of making an implantable matrix configured to fit at or near a target tissue site, the method comprising providing a biodegradable material and applying a ligand to bind the ligand to the biodegradable material, thereby forming the implantable matrix, wherein the implantable matrix is configured such that the ligand binds to a receptor and allows influx of cells into the implantable matrix; and wherein:

the ligand is uniformly disposed throughout the implantable matrix in an amount of 0.4 mg/ml to 10.0 mg/ml so that the ratio of ligand to receptor is from about 0.5 to about 1.5;

the implantable matrix releases the ligand at a rate of 0.2 ng/ml/hour to 20 ng/ml/hour;

the ligand is bone morphogenetic protein-2;

the implantable matrix allows influx of at least progenitor cells, bone cells and/or cartilage cells into the implantable matrix;

the implantable matrix is porous, and at least 50% of the pores have a pore size between 10 μm and 500 μm;

the implantable matrix has a density of 1.6 g/cm$^3$ to 0.05 g/cm$^3$, and the implantable matrix resists compression by 95% or more in one or all directions when a force is applied to the implantable matrix;

the implantable matrix comprises elongated particles; and the implantable matrix further comprises an agent that reduces degradation of the ligand.

2. A method according to claim 1, wherein the ligand remains in or on a surface of the implantable matrix over a period of 3 days to 12 months.

3. A method according to claim 1, wherein the receptor is disposed in progenitor cells, bone cells and/or cartilage cells.

4. A method according to claim 1, wherein the biodegradable material comprises collagen.

5. A method according to claim 1, wherein the biodegradable material comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, resorbable ceramic, bone, collagen, hyaluronic acid, glycine, glutamic acid or a combination thereof.

6. A method according to claim 5, wherein the resorbable ceramic comprises tricalcium phosphate and hydroxyapatite in a ratio of about 80:20 to about 90:10.

7. A method according to claim 1, wherein the agent that reduces degradation of the ligand comprises a serine protease inhibitor.

8. A method according to claim 1, wherein the agent that reduces degradation of the ligand comprises a metalloprotease.

9. A method according to claim 1, wherein the implantable matrix further comprises a film-forming agent.

10. A method according to claim 1, wherein the implantable matrix is seeded with mesenchymal stem cells.

* * * * *